United States Patent [19]

Wolanin

[11] Patent Number: 5,723,442
[45] Date of Patent: Mar. 3, 1998

[54] PEPTIDE DERIVATIVES

[75] Inventor: Donald John Wolanin, Wilmington, Del.

[73] Assignee: Zeneca Inc., Wilmington, Del.

[21] Appl. No.: 43,616

[22] Filed: Apr. 7, 1993

Related U.S. Application Data

[63] Continuation of Ser. No. 519,604, May 7, 1990, abandoned.

[30] Foreign Application Priority Data

May 8, 1989 [GB] United Kingdom .................. 8910550

[51] Int. Cl.$^6$ ........................... A61K 38/06; A61K 38/05
[52] U.S. Cl. ....................... 514/18; 514/19; 530/331; 530/332
[58] Field of Search ........................ 530/331, 332; 514/18, 19

[56] References Cited

U.S. PATENT DOCUMENTS

| | | | |
|---|---|---|---|
| 4,256,761 | 3/1981 | Suh et al. | 514/464 |
| 4,910,190 | 3/1990 | Bergeson et al. | 514/19 |
| 5,164,371 | 11/1992 | Edwards et al. | 514/18 |
| 5,194,588 | 3/1993 | Edwards et al. | 530/331 |
| 5,221,665 | 6/1993 | Skiles | 514/18 |

FOREIGN PATENT DOCUMENTS

| | | |
|---|---|---|
| 0 276 101 | 7/1988 | European Pat. Off. . |
| 0 291 234 | 11/1988 | European Pat. Off. . |
| 0 369 391 | 5/1990 | European Pat. Off. . |
| 2 095 682 | 10/1982 | United Kingdom . |

OTHER PUBLICATIONS

Stein et al, *Biochem.* 26: 2682–2689, 1987.
J. L. Stanton et al., *J. Med. Chem.* (1983) 26, 1267–77.
J. T. Suh et al., *J. Med. Chem.* (1985) 28, 57–66.
S.M. Weldon et al., *FASEB J.* (1990) 4 (4), Abstract 5212.
B. Imperiali and R. H. Abeles, *Biochemistry* (1986) 23, 3760–67.

*Primary Examiner*—Stephen Walsh
*Attorney, Agent, or Firm*—Liza D. Hohenschutz

[57] ABSTRACT

The present invention relates to certain peptide derivatives, as described herein, which are human leukocyte elastase (HLE) inhibitors making them useful whenever such inhibition is desired, such as for research tools in pharmacological, diagnostic and related studies and in the treatment of diseases in mammals in which HLE is implicated, including treatment of tissue degenerative diseases such as pulmonary emphysema. The invention also includes intermediates useful in the synthesis of these peptide derivatives, processes for preparing them, pharmaceutical compositions containing such peptide derivatives and methods for their use.

19 Claims, No Drawings

PEPTIDE DERIVATIVES

This is a continuation of application Ser. No. 07/519,604 filed on May 7, 1990 now abandoned.

The present invention relates to certain peptide derivatives, in particular, certain tripeptidoyl trifluoromethane derivatives, which are human leukocyte elastase (HLE) inhibitors making them useful whenever such inhibition is desired, such as for research tools in pharmacological, diagnostic and related studies and in the treatment of diseases in mammals in which HLE is implicated, including treatment of tissue degenerative diseases such as pulmonary emphysema. The invention also includes intermediates useful in the synthesis of these peptide derivatives, processes for preparing them, pharmaceutical compositions containing such peptide derivatives and methods for their use.

In European Patent Application, Publication Number 189 305 A2 are disclosed a series of peptidoyl trifluoromethane derivatives which are HLE inhibitors. I have now discovered a series of tripeptidoyl trifluoromethane derivatives which contain an N-cyclopentylglycyl group at the $P_2$-position and which unexpectedly possess inhibitory properties against HLE. In addition, the new derivatives have improved solution stability. This is the basis for my invention.

According to the invention there are provided compounds of formula I (formula set out, together with other formulae referred to by Roman numerals, following the Examples) wherein:

A is selected from a group consisting of —CO—, —NH.CO— and —O.CO—;

L is selected from a group consisting of phenylene, (1–6C)alkanediyl, (2–6C)alkenediyl and phenylene(1–3C) alkyl, optionally containing one double bond in the alkyl portion, with the condition that no carbon included in a double bond of an alkenediyl group or included in an optional double bond of a phenylenealkyl group be directly bonded to an oxygen or nitrogen atom of group A; and $R^4$ is selected from a group consisting of acylsulfonamide of formula $R^5.S(O_2).NH.CO$—, acylsulfonamide of formula $R^5.CO.NH.S(O_2)$—, sulfonylurea of formula $R^5.NH.CO.NH.S(O_2)$—, sulfonylurea of formula $R^5.S(O_2)$ .NH.CO.NR$^6$—, and trifluoromethylsulfonamide of formula $CF_3.S(O_2).NH$— wherein $R^5$ is selected from a group consisting of (1–10C)alkyl; trifluoromethyl; (3–10C)cycloalkyl; (6 or 10C)aryl optionally substituted by 1 to 3 members of a group consisting of halogeno, nitro, amino, dimethylamino, hydroxy, methyl, trifluoromethyl, carboxy, phenyl, and [(1–5C)alkylcarbonyl] amino; and an aromatic heterocyclic group defined as herein below in which up to 3 carbons of the aromatic system may bear a substituent group independently selected from a group consisting of halogeno and trifluoromethyl; and $R^6$ is hydrogen or methyl; and the pharmaceutically acceptable base-addition salts thereof.

In this specification, the following definitions are used, unless otherwise described:

Halogeno is fluoro, chloro, bromo or iodo.

Aromatic heterocyclic group means a monocyclic or fused bicyclic ring system of from 5 to 11 atoms containing at least one 5- or 6-membered aromatic ring and consisting of from 1 to 10 carbons and from 1 to 4 heteroatoms each of which is selected independently from a group consisting of oxygen, sulfur, and nitrogen.

Alkyl, alkanediyl, alkenediyl, etc. denote both straight and branched groups.

The radicals $R^4$ and L may contain chiral centers. The present invention includes compounds of formula I wherein chiral centers included in $R^4$ and L are of the R and/or S configurations. The radical L may contain a double bond; the present invention includes compounds of formula I wherein a double bond included in L is of the E and/or Z configuration.

The compounds of the invention of formula I can be viewed as tripeptidoyl trifluoromethane derivatives. In general, the preferred compounds of the present invention are of the naturally occurring L-amino acid configuration at the chiral center identified by * in formula I. The methods of synthesis described below may provide a diastereomeric mixture as a result of the presence of products with both the R and the S configurations at the chiral center identified by # in formula I. While these diastereomers may be separated, it is not necessary to do so. The preferred compounds are those assigned the S configuration at the chiral center identified by #.

As will be appreciated by those skilled in the art, the activity of the individual isomers is not the same, and it is therefore preferred to utilize the more active isomer. The present invention includes both the diastereomeric mixture and the active S and R isomers.

As will be appreciated by those skilled in the art, the trifluoromethyl ketones can exist as solvates, particularly hydrates, as represented by formula II, and these are encompassed by the present invention.

A particular value of $R^5$ when $R^5$ is (1–10C)-alkyl is, for example, methyl, ethyl, propyl, isopropyl, t-butyl or 4-methylpentyl. A particular value of $R^5$ when $R^5$ is (3–10C) cycloalkyl is, for example, cyclopropyl, cyclopentyl, cyclohexyl, norbornyl, or adamantyl. A particular value for $R^5$ when $R^5$ is (6 or 10C)aryl is, for example, phenyl or naphthyl; a particular value for an optional substituent on aryl when the substituent is halogeno is, for example, fluoro, chloro or bromo; and a particular value for an optional substituent on aryl when the substituent is [(1–5C) alkylcarbonyl]amino is, for example, formylamino, acetylamino, 2-methylpropanoylamino or 2,2-dimethylpropanoylamino. A particular value for $R^5$ when $R^5$ is an aromatic heterocyclic group is, for example, furyl, thienyl, pyridyl or pyrimidinyl; and a particular value for an optional substituent when the substituent is halogeno is, for example, fluoro, chloro or bromo.

A particular value for L when L is phenylene is, for example, p-phenylene or m-phenylene. A particular value for L when L is (1–6C)alkanediyl is, for example, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl or pentan-1,5-diyl. A particular value for L when L is (2–6C) alkenediyl is, for example, ethen-1,2-diyl, propen-1,2-diyl, propen-1,3-diyl, buten-1,4-diyl, but-2-en-1,4-diyl, penten-1, 5-diyl or 3,3-dimethylpropen-1,3-diyl. A particular value for L when L is phenylene(1–3C)alkyl is, for example, p-phenylenemethyl, 2-(p-phenylene)ethyl or 2-(p-phenylene)-2-propyl; and when the phenylene-(1–3C)alkyl group contains an optional double bond, a particular value for L is, for example 2-(p-phenylene)ethenyl.

The particular values listed for radicals, substituents and ranges are for illustration only and do not exclude other defined values or other values within defined ranges for the radicals and substituents.

Values for $R^4.L.A$— in formula I of particular interest include for $R^4$: $R^5.S(O_2).NH.CO$—; for L: p-phenylene; and for A: —CO—. A value of $R^5$ of particular interest is 4-chlorophenyl.

Specific compounds of formula I are described in the accompanying Examples. A compound of special interest is: [4-[(4-chlorophenyl)sulfonylaminocarbonyl]benzoyl]-L-valyl-Nα-cyclopentyl-N-[3,3,3-trifluoro-1-(1-methylethyl)-2-oxopropyl]-glycinamide.

The salts of the compounds of formula I include pharmaceutically acceptable base-addition salts such as those derived from alkali metal hydroxides such as sodium hydroxide, alkali metal carbonates and bicarbonates, alkaline earth hydroxides and organic amines. Such salts may be prepared by dissolving the heterocyclic ketone in a mixture of water and a water-miscible organic solvent, adding an aqueous solution of the base and recovering the salt from the aqueous solution.

The compounds of formula I may be made by processes which include processes known in the chemical art for the production of structurally analogous heterocyclic and peptidic compounds. Such processes for the manufacture of a compound of formula I as defined above are provided as further features of the invention and are illustrated by the following procedures in which the meanings of generic radicals are as defined above:

(A) Oxidizing a corresponding alcohol of formula III. Methods which are useful include the use of oxalyl chloride, dimethyl sulfoxide, and a tertiary amine; the use of acetic anhydride and dimethyl sulfoxide; the use of chromium trioxide pyridine complex in methylene chloride; and the use of Dess-Martin periodinane [1,1,1-triacetoxy-2,1-benzoxiodol-3(3H)-one] (method of Dess, D. B. et al.,.J. Org. Chem., 48, 4155–56 (1983)). Generally, a preferred oxidant is Dess-Martin periodinane. An alternative preferred method of oxidation may be the use of potassium permanganate in a basic aqueous solution. When an alcohol of formula III contains a basic nitrogen, it is generally preferable to use an alternative method or to protect the basic nitrogen before oxidation and deprotect it after oxidation to provide the corresponding compound of formula I.

(B) For a compound of formula I wherein $R^4$ has the value $R^5.S(O_2).NH.CO$—, reacting a corresponding compound of formula IV wherein $R^7$ is carboxy (which compound is hereinafter referred to as "acid of formula IV") with a sulfonamide derivative of formula $R^5.SO_2.NH_2$ in the presence of a dehydrating agent or reacting a reactive derivative of an acid of formula IV with a sulfonamide, or a salt thereof, of formula $R^5.SO_2.NH_2$. Thus, for example, a free acid of formula IV may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^5.SO_2.NH_2$ in the presence of a suitable solvent or diluent, for example, dichloromethane, at a temperature in the range of, for example, 0° to 50° C., but preferably at or near ambient temperature.

Alternatively, a reactive derivative of an acid of formula IV, for example, an acid halide (such as the acid chloride), acid anhydride or a mixed acid anhydride (such as that formed from N,N-diphenylcarbamic acid and the acid of formula IV by reaction of the sodium salt of the latter acid with N,N-diphenylcarbamoylpyridinium chloride), may be reacted with an alkali metal salt (such as the lithium, sodium or potassium salt) of the appropriate sulfonamide of formula $R^5.SO_2.NH_2$, conveniently at or near ambient temperature and in a suitable solvent or diluent, for example, tetrahydrofuran, N,N-dimethylformamide or dichloromethane.

(C) For a compound of formula I wherein $R^4$ has the value $R^5.CO.NH.S(O_2)$—, reacting a corresponding compound of formula IV in which $R^7$ has the value $H_2N.S(O_2)$— with an acid of formula $R^5.COOH$ using a similar method to one of those described above in part (B).

(D) For a compound of formula I wherein $R^4$ has the value $R^5.NH.CO.NH.S(O_2)$—, reacting a corresponding compound of formula IV in which $R^7$ has the value $H_2N.S(O_2)$— with an isocyanate of formula $R^5.NCO$. For example, an intermediate of formula IV in which $R^7$ is $H_2N.S(O_2)$— may be treated with phenylisocyanate to provide a corresponding product of formula I in which $R^5$ is phenyl.

(E) For a compound of formula I wherein $R^4$ has the value $R^5.S(O_2).NH.CO.NR^6$—, reacting a corresponding compound of formula IV in which $R^7$ has the value $HNR^6$— with a sulfonylisocyanate of formula $R^5.S(O_2).NCO$; or alternatively, for a compound in which $R^6$ has the value H, reacting a corresponding compound of formula IV in which $R^7$ has the value —NCO with a sulfonamide of formula $R^5.S(O_2).NH_2$. The reaction may be carried out, for example, at room temperature in a suitable inert organic solvent such as tetrahydrofuran or dichloromethane.

(F) For a compound of formula I wherein $R^4$ has the value $CF_3.S(O_2).NH$—, reacting a corresponding amine of formula IV in which $R^7$ has the value $H_2N$— with trifluoromethanesulfonic anhydride, for example, at 0° C. in an inert solvent such as dichloromethane.

(G) For a compound of formula I wherein A has the value —CO—, coupling an acid of formula $R^4.L.COOH$ (or a reactive derivative thereof) with an amino ketone of formula V. For example, the coupling may be carried out using 1-(3-dimethylaminopropyl)-3-ethylcarbodiimide hydrochloride and 4-dimethylaminopyridine or 1-hydroxybenzotriazole in an inert solvent such as tetrahydrofuran. Similarly, a compound of formula I wherein A has the value —NH.CO— or —O.CO— may be prepared from a corresponding amino ketone of formula V using a similar method to one described below for the preparation of a starting material alcohol of formula III from an amino alcohol of formula VII.

It may be desired to optionally use a protecting group during all or portions of the above described processes; the protecting group then may be removed when the final compound or a required starting material is to be formed.

Whereafter, for any of the above procedures, when a pharmaceutically acceptable salt is required, it may be obtained by reaction of the acidic form of a compound of formula I with a base affording a physiologically acceptable cation or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples.

As will be clear to one skilled in the art, a variety of sequences is available for preparation of the starting materials. According to one of the available routes, a key intermediate amino alcohol of formula VII may be prepared as shown in Scheme I (set out following Examples) wherein CBZ represents a benzyloxycarbonyl protecting group and as described in Example 1.

Henry condensation of isobutyl nitrate with trifluoroacetaldehyde ethyl hemiacetal provides the nitro alcohol XI as a mixture of two racemic diastereomers [(2RS,3RS) and (2RS,3SR)]. As is described in Example 1.b., it is preferable to effect a separation of the mixture of racemic diastereomers of formula XI by fractional distillation and crystallization to provide nitro alcohol of formula VI as a substantially pure racemic diastereomer [(2RS,3SR)] substantially free of the other racemic diastereomer [(2RS,3RS)]. Reduction of the nitro group by the preferred method of hydrogenation over 10% (w/w) palladium on carbon catalyst provides an amino alcohol of formula XII, conveniently isolated as the hydrochloride salt, as one racemic diastereomer [(2RS,3RS)] substantially free of the other racemic diastereomer. The amine salt may be used directly for further synthesis. (It will be appreciated by one skilled in the art that, alternatively, the other racemic diastereomer [(2RS, 3RS)] may also be used for the production of compounds of this invention.)

If it is desired to carry out a chiral synthesis of a compound of formula I, amino alcohol of formula XII which is substantially enantiomerically and diastereomerically pure may be obtained by resolution. For example, the free base of the racemic (2RS,3SR) diastereomer of the amino alcohol of formula XII may be resolved by formation of the diastereomeric salts with D-tartaric acid and separation of those salts, for example as described in Example 1.c-1. The salt containing the (2R,3S) isomer of the amino alcohol of formula XII may then be used in further procedures analogous to those of Example 1 to provide an intermediate amino alcohol of formula VII which is substantially enantiomerically pure, and which may be further converted into a product of formula I which is substantially enantiomerically and diastereomerically pure by a method described herein by using methods and conditions which avoid epimerization.

Conversion of an amino alcohol of formula XII into a corresponding alcohol of formula XVI may be carried out by coupling the amino alcohol with an acid of formula XV using a conventional coupling procedure, such as, for example, using 1-(3-dimethylaminopropyl)-3-ethylcarbodiimide hydrochloride and 1-hydroxybenzotriazole in tetrahydrofuran or, especially, by using bis(2-oxo-3-oxazolidinyl)phosphinic chloride and triethylamine in dichloromethane, for example as described in Example 1. An alcohol of formula XVI may be converted into an amino alcohol of formula VII by removal of the CBZ-group using a conventional method, such as, for example, hydrogenolysis over a palladium on carbon catalyst at about 3 bars pressure and ambient temperature in an appropriate solvent such as, for example, ethanol.

An amino alcohol of formula VII may be converted into a starting material of formula III by reacting the amino alcohol of formula VII with an appropriate acylating agent. For example, when A is —CO—, appropriate acylating agents are activated derivatives of acids of formula $R^4$.L.COOH, for example, activated derivatives thereof generated in situ when using conventional coupling reagents, such as, for example, 1-(3-dimethylaminopropyl)-3-ethylcarbodiimide hydrochloride and 1-hydroxybenzotriazole or 4-dimethylaminopyridine, as well as, for example, acid chlorides of formula $R^4$.L.COCl. When A is —NH.CO—, appropriate acylating agents include isocyanates of formula $R^4$.L.NCO. When A is —O—CO—, appropriate acylating agents include chloroformates of formula $R^4$.O.CO.Cl. In general, the acylation is performed in an inert diluent or solvent, such as dichloromethane, tetrahydrofuran or dioxane, and at a temperature in the range of, for example, 0°–60° C. An organic or inorganic base such as triethylamine, 4-methylmorpholine, 4-dimethylaminopyridine, potassium carbonate or sodium hydroxide may also conveniently be used as an acid acceptor when appropriate.

Starting material ketones of formula IV may also be obtained from an intermediate alcohol of formula VII. Thus, for example, for a starting material of formula IV wherein $R^7$ has a value of $R^zO_2C$—, $H_2N.SO_2$—, or $R^6NH$— and $R^z$ has a value defined below, an amino alcohol of formula VII may be converted into a corresponding alcohol of formula VI by using a method analogous to one described above for preparation of a compound of formula III and an analogous reagent, such as, for example $R^7$.L.COOH, $R^7$.L.COCl, $R^7$.L.NCO or $R^7$.L.OCOCl. Then, by using a similar oxidation process to one described in process (A), an alcohol of formula VI may be oxidized to provide a starting material ketone of formula IV. A starting material ketone of formula IV wherein $R^7$ has a value of —NCO may be prepared from a corresponding ketone of formula IV wherein $R^7$ is carboxy by use of a modified Curtius reaction using, for example, diphenylphosphorylazide and triethylamine in benzene or toluene at 80° C. A starting material of formula IV wherein $R^7$ has the value carboxy may be prepared by decomposing a suitable, corresponding ester of formula IV wherein $R^7$ has the value $R^zO_2C$— in which $R^z$ is a conveniently removed acid protecting group, for example, phenyl, benzyl, or (1–6C)alkyl optionally bearing an acetoxy, (1–4C)alkoxy or (1–4C)alkylthio substituent.

A particular value for $R^z$ is, for example, methyl, ethyl, propyl, t-butyl, acetoxymethyl, methoxymethyl, 2-methoxyethyl, methylthiomethyl, phenyl, or benzyl.

It will be appreciated that the decomposition of an ester of formula IV wherein $R^7$ is $R^zO_2C$— may be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Alternatively, in certain circumstances, for example, when $R^z$ is t-butyl, it may be preferred to carry out the decomposition using acid catalysis, for example, by treating an ester of formula IV with, for example, trifluoroacetic acid at a temperature of, for example, 0°–40° C., in a suitable solvent or diluent such as dichloromethane. In addition, when $R^z$ is t-butyl, the decomposition may be performed, for example, by using trimethylsilyl triflate and then water, in a conventional manner. Still further, in certain circumstances, for example, when $R^z$ is benzyl, it may be possible to carry out the decomposition by reductive means, for example, by the use of hydrogen at a pressure of about thee bars in the presence of a suitable catalyst, such as palladium or platinum, conveniently on charcoal as a support.

A starting material amino ketone of formula V may be obtained from a corresponding alcohol of formula XVI via a corresponding ketone of formula VIII. Thus, by using an oxidation procedure similar to one described above in method (A), the alcohol of formula XVI may be oxidized to the corresponding ketone of formula VIII, for example, by using Dess-Martin periodinane. Removal of the N-protecting group from the ketone of formula VIII will then provide the starting material amino ketone of formula V. The protecting group conveniently may be removed using, for example, trifluoromethanesulfonic acid in dichloromethane at room temperature. It is convenient to isolate an amino ketone of formula V so prepared as its crude trifluoromethanesulfonic acid salt and use it directly for the preparation of a corresponding product of formula I. If an amino ketone of formula V is isolated in the form of its free base, it may be preferable to use the material at once because of the limited stability of the free base.

Starting material ketones of formula IV may also be prepared from an amino ketone of formula V using methods analogous to those described above for the preparation of alcohols of formula VI from an alcohol of formula VII.

As will be clear to one skilled in the art, the order of steps in the sequences leading to the starting materials and products of the invention may be altered if appropriate considerations relative to coupling methods, racemization, deprotection methods, etc. are followed.

Inhibition Measurements:

The potency of compounds of the invention to act as elastase inhibitors is initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxysuccinyl-alanyl-alanyl-prolyl-valine-p-nitroanilide as described by Nakajima, K. et al. in *J. Biol. Chem.*, 245, 4027–4032 (1979) and by Teshima, T. et al. in *J. Biol. Chem.*, 257, No. 9, 5085–5091 (1982). The HLE enzyme used in these studies may be obtained from Elastin Products of St. Louis, Mo. or can be purified according to Viscarello, B. R. et al. in *Preparative Biochemistry*, Vol. 13, pages 57–67, (1983) as also described in European Patent Application, Publication Number 189 305 A2. From the thus purified HLE, a standard rate of production of p-nitroaniline was measured at 25° C. spectrophotometrically in the visible spectrum at 410 nanometers with automatic data acquisition from a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

If the peptide derivatives of the present invention are found to be "slow-binding" inhibitors of HLE, special methods of analysis to accurately determine $K_i$ values for their inhibition of HLE are carried out (see Williams, J. W. and Morrison, J. F., *Meth. Enz.* 63, 437 (1979) for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO are added to a 3 milliliter cuvette. The cuvette is stoppered, inverted several times to mix its contents and maintained at (25° C.) in the spectrophotometer. After a period of five minutes to allow the reaction solution to come to thermal equilibrium, 10 microliters of stock enzyme solution are added to the cuvette to initiate the reaction. Duplicate or triplicate runs are done at zero inhibitor concentration and at least three non-zero inhibitor concentrations. $K_i$ values are calculated according to methods outlined in the above reference by Williams and Morrison. The $K_i$ values for selected compounds are less than $10^{-7}$M.

Animal Models

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing 400 μg of human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavagable cells relative to HLE alone.

Compounds of the present invention which were tested exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavagable cells and wet lung weights relative to the administration of HLE alone obtained in the Animal Model test.

According to a further feature of the invention, there are provided pharmaceutical compositions comprising a pharmaceutically effective amount of at least one substituted amide of formula I and a pharmaceutically acceptable diluent or carrier.

The compounds of the present invention may be administered to a warm-blooded animal, particularly a human, in need thereof for treatment of a disease in which HLE is implicated, including treatment of a tissue degenerative disease, in particular for the treatment of emphysema. The preferred mode of administration may be via a powdered or liquid aerosol. In a powdered aerosol, compounds of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a compound of the invention with the remainder of the 20 mg capsule being a pharmaceutically acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the conditions being treated, the weight of the patient and the particular size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy," Lea and Febiger, Philadelphia (1976).

Alternatively, the mode of administration may be oral or parenteral, including subcutaneous deposit by means of an osmotic pump. The compounds of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 ml intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

The invention will now be illustrated by the following non-limiting examples in which, unless stated otherwise:

(i) temperatures are given in degrees Celsius (C); operations were carried out at room or ambient temperature, that is, at a temperature in the range of 18°–25° C.;

(ii) evaporation of solvent was carried out using a rotary evaporator under reduced pressure (600–4000 pascals; 4.5–30 mmHg) with a bath temperature of up to 60° C.;

(iii) flash chomatography was carried out on Merck Kieselgel (Art 9385) [obtained from E. Merck, Darmstadt, W. Germany]; if "acidic silica gel" is indicated, material custom prepared by J. T. Baker Chemical Co., Phillipsburg, N.J., USA, and having a pH of about 6 when slurried in water was used; thin layer chomatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) final products had satisfactory nuclear magnetic resonance (NMR) spectra and were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 80 MHz or 250 MHz using $CDCl_3$, $DMSO-d_6$ or $CD_3OD$ as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: min (minutes), h (hours), v (volume), w (weight), mp (melting point), l [liter(s)], ml (milliliters), g [gram(s)], mg [milligram(s)];

(xi) solvent ratios are given in volume: volume (v/v) terms;

(xii) mass spectra (MS) were run with an electron energy of 70 electron volts in the chemical ionizaton mode using a direct exposure probe; when given, only peaks ten percent of the base peak and larger are reported; and (xiii) when high pressure liquid chromatography (HPLC) data is reported, $t_R$ (retention time) is given in min, FR (flow rate) is given in ml/min, Col A is a Zorbax (trademark) ODS analytical column (4.6 mm×25 cm) and Col B is a Phenomenex (trademark) Zorbax (trademark) C-8 analytical column (4.6 mm×35 cm).

NOMENCLATURE: For uniformity and clarity, "amino acid sequence" type names are used whenever possible. In general, a stereochemical identification as (S) indicates that the product is estimated to contain at least 95% of the (S)-isomer at the center indicated; the absence of an identification of stereochemistry at a chiral center indicates a mixture of isomers which is not necessarily 1:1 at the center indicated.

EXAMPLE 1

[4-[(4-Chlorophenyl)sulfonylaminocarbonyl]benzoyl]-L-valyl-Nα-cyclopentyl-N-[3,3,3-trifluoro-1-(1-methylethyl)-2-oxopropyl]glycinamide (Formula I, A=CO, L=p-phenylene, $R^4=R^5.S(O_2).NH.CO—$, $R^5=4—ClC_6H_4$).

A solution of the alcohol of Example 1.k. (below) (0.47 g) in dichloromethane (40 ml) was treated with Dess-Martin periodinane (0.58 g) followed by trifluoroacetic acid (0.051 ml). The reaction was stirred at room temperature overnight and evaporated. To the residue was added ethyl acetate (80 ml) followed by 50 ml of 1:1 (v:v) saturated $NaHCO_3$:saturated $Na_2S_2O_3$. Stirring was continued until all the solid dissolved. The organic layer was separated, washed (brine), dried ($MgSO_4$), and evaporated. Flash chomatography, eluting with chloroform:methanol:acetic acid (20:1:0.1), gave the title product as a white solid (0.34 g 72%) after overnight drying in a vacuum oven; MS, m/e=715(M+1, $^{35}$Cl), 421, 307, 295(base).

Analysis for $C_{32}H_{38}ClF_3N_4O_7S$:

Calculated: C, 53.76; H, 5.32; N, 7.83; Cl, 4.96; S, 4.48

Found: C, 53.74; H, 5.56; N, 7.41; Cl, 4.66; S, 4.84

The alcohol used in Example 1 was prepared as follows:

a. 2-Methyl-1-nitropropane.

A 5-liter, 3-necked, round-bottomed flask was equipped with a mechanical stirrer, thermometer, addition funnel and $N_2$ inlet. The flask was charged with $AgNO_2$ (1006.8 g) in ether (2.5 liter), and isobutyl iodide (927.2 g) was placed in the addition funnel. Both the flask and the addition funnel were wrapped in aluminum foil to protect the reaction from light. After the stirred suspension was cooled to approximately 5° C. (ice bath), dropwise addition of the iodide over a 2 h period was begun. The reaction temperature was maintained at or less than 5° C. thoughout the course of the addition. When the addition was complete, the reaction vessel was packed in ice and allowed to warm slowly to room temperature overnight. NMR analysis of an aliquot taken from the reaction mixture after 48 h of stirring demonstrated that all of the isobutyl iodide had been consumed. The reaction mixture was filtered though diatomaceous earth to remove silver salts and the filter cake was washed with ether (3×500 ml). The combined filtrates were dried ($MgSO_4$), filtered and partially evaporated (bath temp=35° C.) to about 600 ml. Fractional distillation (atmospheric pressure) (caution: potentially explosive) gave the purified nitro compound (350.4 g, 68% yield); bp 135°–142° C.

(2RS,3SR)-4-Methyl-3-nitro-1,1,1-trifluoro-2-pentanol (Formula XI)

EXPLOSION WARNING: The nitro alcohol of formula XI and its nitroalkane precursor are potentially explosive. The compound of formula XI is thermally unstable and, on a small scale, has been observed to decompose with considerable violence in the range 170°–180° C. Samples of the material have been safely distilled at reduced pressure (95°–105° C./2.0 torr, 67 Pa). Recommendations for safe distillation include keeping the oil bath below 110° C., never taking still residues below 15% of the original crude volume, and conducting the distillation behind a safety screen.

A 3-liter, 3-necked, round-bottomed flask equipped with a mechanical stirrer and $N_2$ inlet was charged with $K_2CO_3$ (470.0 g), the product of Example 1.a. (350.0 g) and finally trifluoroacetaldehyde ethyl hemiacetal (708.0 g). The mixture was vigorously stirred at room temperature for 76 h, at which time NMR demonstrated the nearly complete consumption of the nitroalkane. The reaction mixture was diluted with dichloromethane and filtered. The filtrate was treated with aqueous HCl until pH=3. The layers were separated and the aqueous layer was washed with dichloromethane (500 ml). The combined dichloromethane portions were washed with water (1 liter) and brine (1 liter). Drying ($MgSO_4$) and evaporation gave 854.6 g of crude product as a yellow oil. NMR showed the two diastereomeric nitro alcohols (present in the ratio of about 3:1 as quantified by integration of the alcohol protons, which consistently appear in the range δ6.0–6.5 when run in acetone-$d_6$) contaminated by solvents and small amounts of starting materials.

Distillation at reduced pressure gave the following fractions:

|   | Weight  | bp (pressure)                        |                |
|---|---------|--------------------------------------|----------------|
| A | 191.7 g | 42° C.C.–50° C. (atmospheric)        | [S.M. + solvents] |
| B | 34.8 g  | 35° C. (133 Pa)–45° C. (67 Pa)       |                |
| C | 213.6 g | 45° C. (67 Pa)–95° C. (200 Pa)       |                |
| D | 337.8 g | 95° C. (200 Pa)–105° C. (267 Pa)     |                |
| E | 114.0 g | trap volatiles                       |                |

To simplify purifications in subsequent synthetic steps, an effort was made at this point to obtain the major diastereomeric pair in a substantially pure state and to advance only this material though the sequence. The major diastereomeric pair crystallizes from the mixture of diastereomers, as well as from cold pentane, to yield colorless needles. Thus, fraction C from the above distillation was allowed to crystallize overnight in a refrigerator. The product was collected, washed with cold pentane and dried for several hours in a vacuum oven (Caution! This material is somewhat volatile and significant quantities can be lost under extended vacuum treatment) to give 52.0 g of substantially pure material. The fractions known (by NMR) to contain significant quantities of the desired isomer were repetitively treated in this fashion (and redistilled to provide new fractions further enriched in the desired diastereomer) to eventually obtain a total of 197.7 g of substantially pure nitro alcohol. This amount represents the type of work done, but it does not reflect the upper limit of the yield.

c. (2RS,3SR)-3-Amino-4-methyl-1,1,1-trifluoro-2-pentanol hydrochloride salt (Formula XII.HCl).

Anhydrous ethanol (232 ml) was added to 10% (w/w) palladium on carbon catalyst (2.30 g) under $N_2^*$. The product of Example 1.b. (22.93 g) was added and the resultant mixture was hydrogenated overnight on a shaker at about 3.7 bar. Catalyst was removed by filtration though diatomaceous earth. The filter cake was then washed with ethanol. HCl gas was bubbled though the combined filtrates until approximately 8 g was absorbed. The solution was evaporated and the resultant residue was evaporated several times from ether to obtain a white solid. The solid was washed with ether and dried overnight in a vacuum oven to yield 20.79 g (88%) of amine hydrochloride; with slow heating the material softened at 90° C. and melted at 118° C.–120° C.; when a sample was plunged into a bath preheated to 110° C., it melted instantaneously. *Less active catalysts (e.g., 10% Pd/BaSO$_4$, wet 10% Pd/C) or insufficient reaction times may lead to the production of one or more by-products.

c-1. (2R,3S)-3-Amino-1,1,1-trifluoro-4-methyl-2-pentanol D-tartaric acid salt. (Formula XII. D-tartaric acid).

Amine hydrochloride (20 g) generated as in Example 1.c. was dissolved in $H_2O$ and neutralized with solid $NaHCO_3$. The aqueous solution was extracted several times with dichloromethane. The combined extracts were dried ($Na_2SO_4$) and concentrated to yield the amine free base (14.04 g) as a white solid. This material was combined with D-tartaric acid (12.31 g) in boiling anhydrous ethanol (100 ml), and the resultant cloudy solution was filtered hot though filter paper. The solution was first cooled slowly to room temperature overnight and then placed in the refrigerator for several hours. Precipitate was collected on a fritted funnel, washed with cold ethanol, and dried overnight in a vacuum oven at 40° C. A sample of the dried white solid (4.56 g) melted at 127°–130° C. Most of this material (4.05 g) was dissolved in boiling ethanol (20 ml), and the solution was slowly cooled to room temperature. The white gel-like solid which deposited was collected on a sintered glass funnel and washed with several portions of ethanol. Vacuum oven drying at 40° C. for several hours gave a white solid, mp, 132°–134° C.

d. N-Cyclopentylglycine t-butyl ester (Formula XIII).

A solution of t-butyl bromoacetate (102.43 g) in tetrahydrofuran (100 ml) was added dropwise to a stirred solution of cyclopentylamine (56.21 g) and triethylamine (105 ml, about 76 g) in tetrahydrofuran (500 ml) maintained in the temperature range –5° C. to 0° C. The stirred reaction mixture was allowed to warm to room temperature overnight. The white solid triethylamine hydrobromide was removed by filtration, and the filter cake washed thee times with ethyl acetate. The organic filtrate was evaporated, and the residue was partitioned between water and ethyl acetate. The separated organic layer was washed (water, brine), dried ($MgSO_4$), and evaporated to give a residue which was purified by fractional distillation to yield the product as a colorless liquid (76.43 g); bp 54°–65° C. (49 Pa); TLC, $R_f$=0.18, hexane:ethyl acetate (9:1); MS, m/e=200(M+1), 172, 145, 144(base), 142, 98, 76.

e. Benzyloxycarbonyl-L-valyl-N-cyclopentylglycine t-butyl ester (Formula XIV).

To a solution of N-benzyloxycarbonyl-L-valine (50.0 g) and N-cyclopentylglycine t-butyl ester (39.8 g) in dichloromethane (1.3 liter), stirred under nitrogen and cooled in an ice bath to 0°–5° C., was added triethylamine (44.5 g) then bis(2-oxo-3-oxazolidinyl)phosphinic chloride (56.0 g) at 0° C. The stirred mixture was allowed to warm to room temperature overnight before it was evaporated. After the residue was partioned between water (1 liter) and ethyl acetate (1 liter), the ethyl acetate solution was washed (1N hydrochloric acid (twice), water, saturated sodium bicarbonate, brine), dried ($MgSO_4$) and evaporated. The residue was purified by flash chromatography, eluting with ethyl acetate:dichloromethane (0:100, 5:95, 10:90 and 25:75, successively). A first, mixed fraction was rechromatographed and the product obtained combined with the product obtained from the first chromatography to afford the ester (73.4 g; 85%); TLC, $R_f$=0.30, ethyl acetate:dichloromethane (5:95); MS, m/e=433 (M+1), 377, 325, 269, 234, 206, 162, 144 91(base).

f. Benzyloxycarbonyl-L-valyl-N-cyclopentylglycine (Formula XV).

To a solution of benzyloxycarbonyl-L-valyl-N-cyclopentylglycine t-butyl ester (73.4 g) in dichloromethane (250 ml), stirred under nitrogen and cooled in an ice bath, was added trifluoroacetic acid (250 ml). After about 5 min the ice bath was removed, and the stirred reaction mixture was allowed to warm to room temperature. After 2.5 h, when TLC indicated complete reaction, the mixture was partially evaporated, removing the dichloromethane and most of the trifluoroacetic acid. The liquid residue was then poured into vigourously stirred ice water, and the resulting mixture of the gummy white solid and aqueous solution was extracted with dichloromethane. The dichloromethane solution was washed (water), diluted with toluene, and evaporated at about 30° C. After several dilutions with toluene, and evaporations to remove traces of water and trifluoroacetic acid, the residue was flash chromatographed on acidic silica gel, eluting with methanol:ethyl acetate:dichloromethane (gradient, 0:0:100, 0:5:95, 0:10:90, 0:25:75, 5:25:70 and 10:25:65, successively) to afford the acid as a white foam (60.4 g, 95%); TLC, $R_f$=0.49, ethyl acetate:dichloromethane:acetic acid (50:50:1); MS, m/e=337(M+1), 359, 225, 91(base).

g. (1RS,2SR)-Benzyloxycarbonyl-L-valyl-Nα-cyclopentyl-N-[3,3,3-trifluoro-2-hydroxy-1-(1-methylethyl)propyl]glycinamide (Formula XVI).

4-Methyl morpholine (0.22 ml) was added to a solution of (2RS,3SR)-3-amino-4-methyl-1,1,1-trifluoro-2-pentanol hydrochloride salt (0.40 g) in dry tetrahydrofuran (5 ml). This mixture and 1-hydroxybenzotriazole (0.26 g) were added to a solution of benzyloxycarbonyl-L-valyl-N-cyclopentylglycine (0.72 g) in dry tetrahydrofuran (60 ml). The reaction mixture was cooled to –30° C., and 1-(3-dimethylaminopropyl)-3-ethylcarbodiimide hydrochloride (0.37 g) was added. Stirring was continued for 1 h at –30° C., and the mixture was then warmed to room temperature overnight. The mixture was evaporated, and the residue was partitioned between water and ethyl acetate. The organic layer was washed (10% HCl, saturated NaHCO₃, water, brine), dried (MgSO₄) and evaporated. Flash chomatography, eluting with chloroform:methanol (60:1), gave the purified alcohol as a white foam (0.73 g, 81%) after overnight drying in a vacuum oven; TLC, $R_f$=0.33, chloroform:methanol (40:1); MS, m/e=530(M+1), 512, 359, 297, 120, 107, 91(base).

h. (1RS,2SR)-L-Valyl-Nα-cyclopentyl-N-[3,3,3-trifluoro-2-hydroxy-1-(1-methylethyl)propyl]glycinamide (Formula VII).

A mixture of (1RS,2SR)-benzyloxycarbonyl-L-valyl-Nα-cyclopentyl-N-[3,3,3-trifluoro-2-hydroxy-1-(1-methylethyl)propyl]glycinamide (0.45 g) and 10% (w/w) palladium on carbon (0.22 g) in ethanol (10 ml) was stirred under hydrogen at atmospheric pressure until all the starting material was consumed. Catalyst was removed by filtration though a column of diatomaceous earth. The filtrate was evaporated and dried overnight under high vacuum to yield the amino alcohol as a light grey solid (0.34 g; 89%); TLC, $R_f$=0.21, chloroform:methanol (40:1); MS, m/e=396-(M+1), 378, 297 (base), 225, 100, 98.

i. 1,1-Dimethylethyl 4-[(4-chlorophenyl)sulfonylaminocarbonyl]benzoate.

A 5-liter, 3-necked, round-bottomed flask was equipped with a mechanical stirrer and nitrogen inlet. dichloromethane (2 liters) was placed in the reaction flask and terephthalic acid mono-t-butyl ester (127.5 g), 4-dimethylaminopyridine (70.06 g), and 4-chlorobenzenesulfonamide (110.04 g) were added in that order using dichloromethane (400 ml) to wash down the solids. 1-(3-Dimethylaminopropyl)-3-ethylcarbodiimide hydrochloride (110.10 g) was added in portions over 10 min using dichloromethane (100 ml) to wash down the solid. After the reaction mixture was stirred overnight at room temperature, it was evaporated. The residue was partioned between ethyl acetate and water. The organic solution was washed (20% (w/v) aqueous citric acid, saturated aqueous NaHCO₃, brine), dried (Na₂SO₄), and evaporated to a white solid. After drying in a vacuum oven at 50° C., the ester (227 g, 100%) was obtained in a sufficiently pure state to be used directly for the next step; TLC, $R_f$=0.43, methanol:chloroform (15:85). (Further purification was possible by recrystallization from ethanol:water; mp above 300° C.).

j. 4-[(4-Chlorophenyl)sulfonylaminocarbonyl]benzoic acid.

A 3-liter, 3-necked, round bottomed flask was equipped with a mechanical stirrer and a CaCl₂ drying tube. Trifluoroacetic acid (1300 g) was added and cooled to 0° C., and the product of Example 1.i. (79.5 g) was added. Initially, the solid dissolved, giving a clear solution. After 10–15 min, a heavy precipitate of product formed; and it was difficult to stir the reaction mixture. Vigorous stirring with the mechanical stirrer was essential to drive the reaction to completion. The reaction mixture was stirred at 0°–5° C. for 1 h before it was poured onto 1500 ml of ice/water and stirred for 2 h. The resulting solid was filtered and dried. The white solid (61.5 g, 91%) obtained was recrystallized from 1600 ml absolute ethanol/1600 ml water to yield the acid (54 g, 80%) as white needles; mp 286°–288° C.; TLC, $R_f$=0.7, methanol:chloroform:acetic acid (10:90:1).

k. (1RS,2SR)-[4-[(4-Chlorophenyl)sulfonylaminocarbonyl]benzoyl]-L-valyl-Nα-cyclopentyl-N-[3,3,3-trifluoro-2-hydroxy-1-(1-methylethyl)propyl]glycinamide (Formula III, A=CO, L=p-phenylene, $R^4=R^5.S(O)_2.NH.CO$—, $R^5$=4—ClC₆H₄).

A solution of the acid of Example 1.j. (0.28 g), the amino alcohol of Example 1.h. (0.33 g) and 1-hydroxy benzotriazole (0.11 g) in dry tetrahydrofuran (10 ml) was cooled to –30° C. and treated with 1-(3-dimethylaminopropyl)-3-ethylcarbodiimide (0.16 g). The reaction was stirred for 1 h at –30° C. and was then warmed to room temperature overnight. The mixture was evaporated and the residue was partitioned between water and ethyl acetate. The organic layer was washed (10% HCl, brine), dried (MgSO₄), and evaporated. The residue was purified by flash chromatography, eluting with chloroform:methanol:acetic acid (100:1:0.5), to yield the alcohol as a white solid (0.49 g, 86%) after overnight drying under high vacuum; TLC, $R_f$=0.39, chloroform:methanol:acetic acid (100:1:0.5); MS, m/e=717(M+1, ³⁵Cl), 699, 421, 297 (base).

FORMULAE

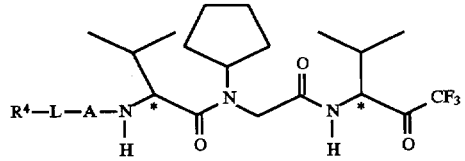

I

-continued
FORMULAE
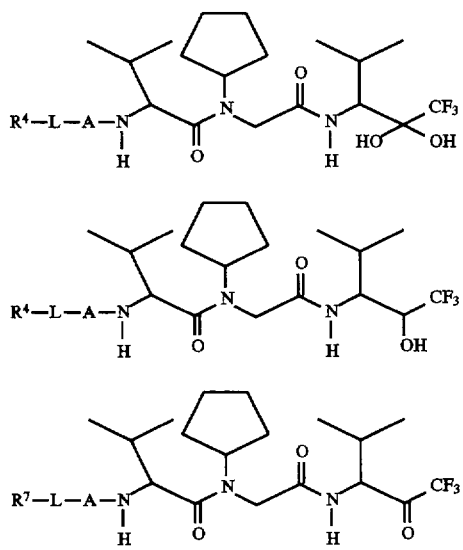
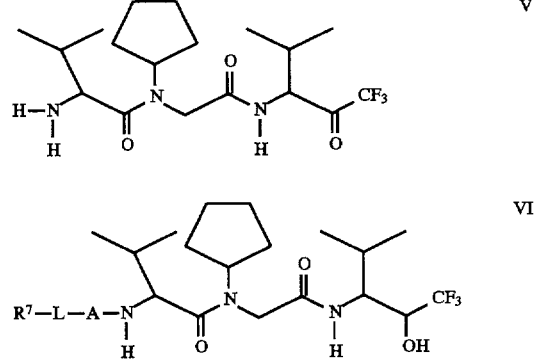
SCHEME I
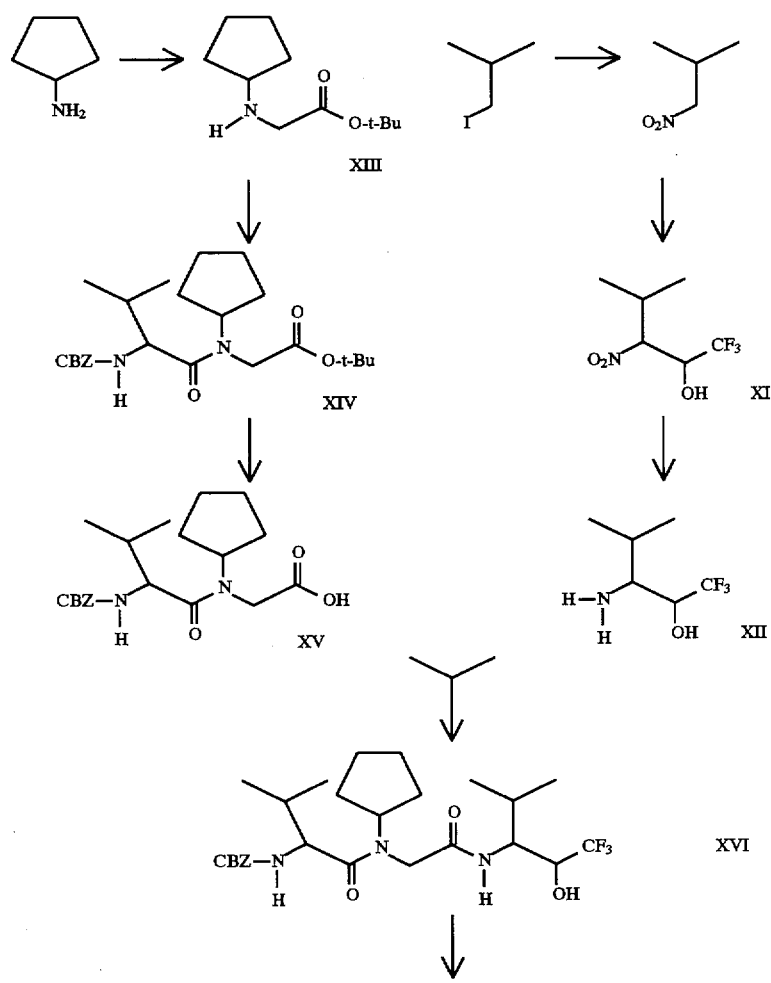

-continued
SCHEME I

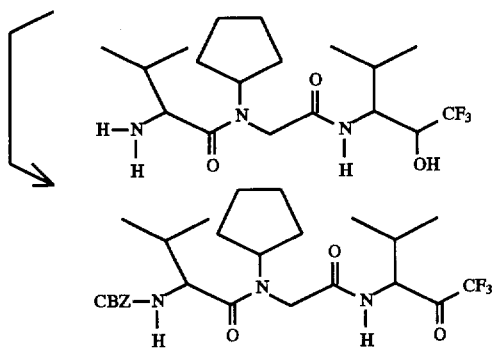

What is claimed is:

1. A compound of formula I

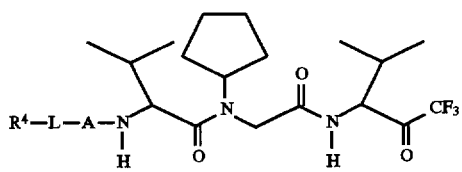

wherein:

A is selected from a group consisting of —CO—, —NH.CO— and —O.CO—;

L is selected from a group consisting of phenylene, (1–6C)alkanediyl, (2–6C)alkenediyl and phenylene (1–3C)alkyl, optionally containing one double bond in the alkyl portion, with the condition that no carbon included in a double bond of an alkenediyl group or included in an optional double bond of a phenylene-alkyl group be directly bonded to an oxygen or nitrogen atom of group A; and $R^4$ is selected from a group consisting of acylsulfonamide of formula $R^5.S(O_2).NH.CO$—, acylsulfonamide of formula $R^5.CO.NH.S(O_2)$—, sulfonylurea of formula $R^5.NH.CO.NH.S(O_2)$—, sulfonylurea of formula $R^5.S(O_2).NH.CO.NR^6$—, and trifluoromethylsulfonamide of formula $CF_3.S(O_2).NH$— wherein $R^5$ is selected from a group consisting of (1–10C)alkyl; trifluoromethyl; (3–10C)cycloalkyl; (6 or 10C)aryl optionally substituted by 1 to 3 members of a group consisting of halogeno, nitro, amino, dimethylamino, hydroxy, methyl, trifluoromethyl, carboxy, phenyl, and {(1–5C)alkylcarbonyl}amino; and an aromatic heterocyclic group in which up to 3 carbons of the aromatic system may bear a substituent group independently selected from a group consisting of halogeno and trifluoromethyl; and $R^6$ is hydrogen or methyl; or a pharmaceutically acceptable base-addition salt thereof.

2. A compound as claimed in claim 1 wherein:

$R^5$ is methyl, ethyl, propyl, isopropyl, t-butyl, 4-methylpentyl, cyclopropyl, cyclopentyl, cyclohexyl, norbornyl, adamantyl, phenyl or naphthyl, which phenyl or naphthyl may optionally bear a fluoro, chloro, bromo, formylamino, acetylamino, 2-methylpropanoylamino or 2,2-dimethylpropanoylamino substituent; or $R^5$ is furyl, thienyl, pyridyl or pyrimidinyl, which heterocyclic group may optionally bear a fluoro, chloro or bromo substituent; and L is p-phenylene, m-phenylene, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl, pentan-1,5-diyl, ethen-1,2-diyl, propen-1,2-diyl, propen-1,3-diyl, buten-1,4-diyl, but-2-en-1,4-diyl, penten-1,5-diyl, 3,3-dimethylpropen-1,3-diyl, p-phenylenemethyl, 2-(p-phenylene)ethyl or 2-(p-phenylene)-2-propyl, or 2-(p-phenylene)ethenyl.

3. A compound as claimed in claim 2 wherein $R^4$ is $R^5.S(O_2).NH.CO$—; L is p-phenylene; and A is —CO—.

4. A compound as claimed in claim 1, 2 or 3 wherein $R^5$ is 4-chlorophenyl.

5. A pharmaceutically acceptable base-addition salt as claimed in claim 1 which is a sodium salt.

6. A pharmaceutical composition comprising a compound of any one of claim 1 in an amount sufficient to inhibit human leukocyte elastase in a living mammal in association with a pharmaceutically acceptable diluent or carrier.

7. A pharmaceutical composition as claimed in claim 6 wherein said composition is in the form of a liquid or powdered aerosol.

8. A method of inhibiting the action of leukocyte elastase in a mammal requiring such treatment comprising administering to said mammal an effective amount of a compound of claim 1.

9. A method of treating emphysema in a mammal comprising administering to the mammal a pharmacologically effective amount of a compound of claim 1.

10. A compound of formula III

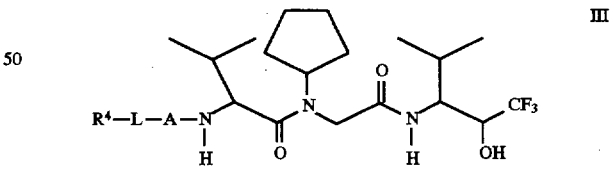

wherein A, L and $R^4$ have any of the meanings defined in claim 1.

11. A compound of formula IV

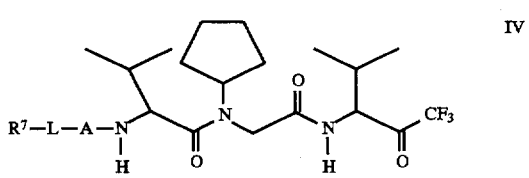

wherein A and L have any of the meanings defined in claim 1 and wherein $R^7$ is selected from a group consisting of carboxy, $H_2N.S(O_2)$—, $HNR^6$—, and —NCO and wherein $R^6$ is hydrogen or methyl.

12. The compound [4-[(4-chlorophenyl)sulfonylaminocarbonyl]-benzoyl]-L-valyl-N$\alpha$-cyclopentyl-N-[3,3,3-trifluoro-1-(1-methylethyl)-2-oxopropyl]glycinamide, or a pharmaceutically acceptable base-addition salt thereof.

13. A pharmaceutically acceptable base-addition salt as claimed in claim 12 which is a sodium salt.

14. A pharmaceutical composition comprising the compound of claim 12, or a pharmaceutically acceptable salt thereof, in an amount sufficient to inhibit human leukocyte elastase in a living mammal in association with a pharmaceutically acceptable diluent or carrier.

15. A pharmaceutical composition as claimed in claim 14 wherein said composition is in the form of a liquid or powdered aerosol.

16. A method of inhibiting the action of leukocyte elastase in a mammal requiring such treatment comprising administering to said mammal an effective amount of the compound of claim 12 or a pharmaceutically acceptable salt thereof.

17. A method of treating emphysema in a mammal comprising administering to the mammal a pharmacologically effective amount of a compound of claim 12 or a pharmaceutically acceptable salt thereof.

18. A compound of formula III

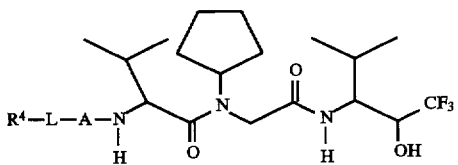

wherein $R^4$ is $R^5.S(O_2).NH.CO$—, A is —CO—, L is p-phenylene, and $R^5$ is 4-chlorophenyl.

19. A compound of formula IV

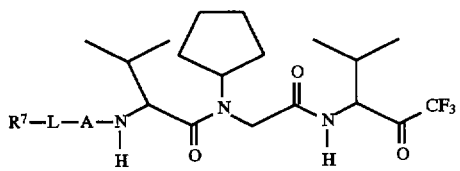

wherein $R^7$ is carboxy, L is p-phenylene, and A is —CO—.

* * * * *